(12) United States Patent
Hedrick

(10) Patent No.: US 6,416,954 B1
(45) Date of Patent: Jul. 9, 2002

(54) MODULATING TH2 CELL LEVELS VIA VMIP-I/CCR8 INTERACTION

(75) Inventor: Joseph A. Hedrick, South River, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/496,675

(22) Filed: Feb. 3, 2000

Related U.S. Application Data (60) Provisional application No. 60/119,033, filed on Feb. 8, 1999.

(51) Int. Cl.[7] ............. G01N 33/50; A61K 39/395; C07K 16/28
(52) U.S. Cl. ............. 435/7.1; 530/351; 530/388.23; 530/388.22; 424/85.1; 424/143.1; 424/144.1; 435/7.21; 435/69.52; 436/501
(58) Field of Search ................. 435/7.1, 7.21, 435/69.52; 436/501; 530/351, 388.23, 388.22; 424/85.1, 143.1, 144.1

(56) References Cited

FOREIGN PATENT DOCUMENTS

WO    WO-99/25734    * 5/1999 ........... C07K/14/00

OTHER PUBLICATIONS

Bingisser RM et al. Swiss Med Wkly Apr. 7, 2001, vol. 131, pp. 17–19. Immunomodulating mechanisms in the lower respiratory tract: nitric oxidemediated interactions between alveolar macrophages, epithelial cells, and t cells.*

Jyonouchi H et al. J Nutr. Apr., 2001, vol. 131, pp. 1165–1170. Dietary ribonucleotide modulate type 1 and type 2 T–helper cell responses against ovalbumin in young BALB/cJ mice.*

Newton C et al. Adv Exp Med Biol 1998, vol. 437, pp. 207–214. The role of macrophages in THC–induced alteration of the cytokine network.*

Boshoff, C. et al., "Angiogenic and HIV–Inhibitory Functions of KSHV–Encoded Chemokines," 1997, *Science*, 278.

Moore, Patrick S., et al., "Molecular Mimicry of Human Cytokine and Cytokine Response Pathway Genes by KSHV," 1996, *Science*, 274.

Horuk, Richard, The CC Chemokine I–309 Inhibits CCR8–dependent Infection by Diverse HIV–1 Strains, 1998, *Journal of Biological Chemistry*, 273:1 pp. 386–391.

Sozzani, S., "The Viral Chemokine Macrophage Inflammatory Protein–II Is a Selective Th2 Chemoattractant," 1998, *Blood*, 92:11 pp. 4036–4039.

* cited by examiner

Primary Examiner—Yvonne Eyler
Assistant Examiner—Sarada Prasad
(74) Attorney, Agent, or Firm—Immac J. Thampoe; Jaye P. Mclaughlin; Michael G. Biro (57) ABSTRACT

The present invention relates to the agonist properties of vMIP-I for the chemokine receptor CCR8 as expressed on Th2 cells. Methods of modulating a physiological signal specific to Th2 cells comprising contacting these cells with vMIP-I, agonists and antagonists thereof are disclosed. Methods for treating disease using CCR8 antagonists are also provided. The modulation of the Th2 cell populations through the vMIP-I/CCR8 interaction provides a new means for diagnosing and treating specific disease states and immunologic conditions.

6 Claims, 2 Drawing Sheets

MODULATING TH2 CELL LEVELS VIA VMIP-I/CCR8 INTERACTION

This application claims priority to U.S. Provisional Application No. 60/119,033, filed Feb. 8, 1999.

FIELD OF THE INVENTION

The present invention relates to the interaction between vMIP-I and CCR8 receptor and the use of these molecules as well as agonists and antagonists thereof in modulating Th1 balance and the immune response.

BACKGROUND OF THE INVENTION

The chemokines are a sub-family of chemoattractant cytokines that were classically characterized by their ability to mediate leukocyte trafficking by binding to specific G-protein linked seven transmembrane spanning receptors, or GPCRs. Chemokines are divided into four groups based on the primary sequence of the first two cysteines: the CXC, CC, C, and the newly discovered, CX3C families. The CXC and C families are effective predominantly on neutrophils and lymphocytes, respectively. The CC chemokines are preferentially effective on macrophages, lymphocytes, and eosinophils.

Only about half of the chemokines have been paired to respective receptors. Some appear to bind to more than one receptor. The matching of orphan receptors with the many chemokines is an ongoing process. The matching of the ligands with receptors often provide useful insight into the physiological functions of the individual chemokines.

The genome of the human herpesvirus 8 (HHV8), a gammaherpesvirus linked to the etiology of Kaposi's sarcoma (KS) [Moore, et al., *J. Virol.* 70:549–558 (1997)] encodes several chemokine-related proteins including a constitutively active G-protein coupled chemokine receptor (vGPCR) that bind several CC and CXC chemokines and three viral chemokines, vMIP-I, vMIP-II and vMIP-III [Moore, et al., *Science* 274:1739–1744 (1996); Arvanitakis, *Nature* 385:347–350 (1997); Nicholas, et al., *J. Natl. Cancer Inst. Monogr.* 23:79–88 (1998); Nicholas, et al., *Nat. Med.* 3:287–292 (1997)]. In addition to its association with KS, HHV8 has also been suggested to play a role in the pathology of primary effusion lymphoma (PEL) [Cesarman, et al., *Am. J. Pathol.* 149:53–57 (1996); Nador, et al., *Blood* 88:645–656 (1996)]. The virus has also recently been linked to the development of multiple myeloma [Rettig, et al., *Science* 276:1851–1854 (1997)]. Expression of the HHV8 GPCR in rodent fibroblasts leads to a proliferative phenotype, suggesting a role for this constitutively active chemokine receptor in tumorigenesis [Arvanitakis, et al., *Nature* 391:86–89 (1998)].

There is a need for understanding the role of these chemokine-related proteins in HHV8 replication and the pathogenesis of HHV8-related disease states, and generally for regimes for the treatment of viral disease and associated pathology.

SUMMARY OF THE INVENTION

The present invention fulfills this need by providing materials and methods for treating disease states associated with immune dysfunction. The invention is based upon the surprising discovery that the vMIP-I is an agonist of the chemokine receptor CCR8, a receptor located on activated Th2 cells.

One object of the present invention is to provide a means for modulating the balance of Th1 and Th2 cells in an animal using the vMIP/CCR8 interaction. Such modulation includes increasing and decreasing the level of Th2 cells in order to treat various disease states.

Another object of the present invention provides a new method of treating patients for various immune related disorders and diseases using the vMIP/CCR8 interaction One aspect of the invention provides a method of modulating a physiological signal specifically to activated Th2 cells. The method comprises contacting activated Th2 cells with vMIP-1, or a vMIP-1 analog or antagonist. The modulating may be blocking,for example, by contacting with a vMIP-I antagonist, e.g., an antibody. Alternatively, the modulating may be inducing with an agonist,such as, by contacting with a CCR8 signaling ligand, e.g., vMIP-I or a vMIP-I signalling analog. The modulating may be directing a response between a Th1 and Th2 response, where the contacting is with vMIP-I, a vMIP-I antagonist or vMIP-I signaling agonist. The physiological signal may be a proliferation, apoptosis, or differentiation signal. The contacting may be in combination with another chemokine or cytokine agonist or antagonist, including IL-12, an IL-12 antagonist, IL-1γ, or an IL-1γ antagonist.

Another aspect of the invention provides methods for diagnosing and/or treating a patient infected with a virus comprising utilizing a vMIP-I antagonist, such as, but not limited to, blocking monoclonal antibodies raised against vMIP-I, a modified vMIP-I peptide or a small molecule antagonist for vMIP-I. These entities block the interaction between vMIP-1 and CCR8, or prevent appropriate signaling through CCR8. This, in turn, blocks the skewing of host responses toward a Th2 phenotype thus making treatment of virus-mediated tumors more effective and/or block anti-apoptotic effects of CCR8 again leading to more effective treatment of such tumors. The knowledge of the vMIP-I/CCR8 interaction also makes available as treatments for viral infection other agents that block this interaction. For example, CCR8 antagonists, I-309 (natural ligand) antagonists and other CCR8 ligand antagonists can be used in the same way as a vMIP-I antagonist to block the vMIP-I/CCR8 interaction.

Still another aspect of the invention provides methods for skewing an immune reponse toward a Th2 phenotype, such as, for example in the treatment of auto-immune diseases (principally Th1 in nature) in which skewing to Th2 lessens disease severity and/or improves the performance of a co-therapy, and in the treatment of bacterial/parasite infections, where the immune response is principally Th2 in nature. In the latter case, vMIP-I or signal agonists thereof increases effectiveness of a Th2 response leading to more rapid eradication of these pathogens.

DETAILED DESCRIPTION OF THE INVENTION

All references cited herein are incorporated in their entirety by reference.

I. General

The present invention is based, in part, upon the surprising discovery that vMIP-I is an agonist of the chemokine receptor CCR8. The human CCR8 receptor has been known under the names TerI [Napolitano et al., (1996), *J. Immunol.* 157:2759–2763 (1996)] ChemR1 [Samson et al., (1996), *Genomics* 36:522–526], and CKR-L1 [Zabellos et al., *Biochem. Biophys. Res. Commun.* 846–853 (1996)] for some time. See GenBank accession numbers AF005210 (partial) and U45983. Until recently, the distribution of the CCR8 receptor had been characterized as lymphoid specific, and particularly to the thymus [Napolitano et al., *J. Immunol.*, 157:2759–2763 (1996)]. Recently, CCR8 has been shown to be preferentially expressed on human and mouse Th2 cells. This discovery was disclosed and claimed in a U.S. patent application Ser. No. 09/190,434, the disclosure of which is hereby fully incorporated by reference. The natural human CCR8 ligand has since been shown to attract Th2-polarized T cells in vitro with considerable vigor [Zingoni et al., *J. Immunol.* 161: 547–51 (1998)].

The ligand for the CCR8 chemokine receptor has been identified in humans as the I-309 protein [Roos et al., *J. Biol. Chem.* 272:17251–17254 (1997); Tiffany, et al, *J. Exp. Med.* 186:165–170 (1997); GenBank Accession Numbers M57502 and M57506], and in mouse as the TCA-3 protein [GenBank Accession Numbers M17957 and X52401]. Van Snick, et al. have reported that I-309 can block dexamethasone-mediated apoptosis of the BW5147 thymoma [Van Snick, et al., *J. Immunol.* 157:2570–6 (1996)], suggesting a role for CCR8 in mediating this event. vMIP-I has now been shown to desensitize CCR8 to subsequent signaling by I-309 and to compete with $^{125}$I-I309 for CCR8 binding.

The activity of vMIP-I as a CCR8 agonist indicates that its expression by HHV8 is part of a viral program to manipulate the Th1/Th2 balance of the host immune response. This finding has led to the present invention of vMIP-I or analogs thereof, as well as other CCR8 agonists or antagonists, and their use as therapeutics in the treatment of viral infections and related diseases, as well as non-virally induced disease states involving a Th1 or Th2 response.

The vMIP-I-CCR8 interaction also finds a role in apoptosis. vMIP-I may be utilized by viruses to prevent apoptosis of a CCR8+ cell population. This may be significant to tumorigenesis in vivo or may serve to extend the life of CCR8+ cells.

The present invention is useful in the treatment of medical conditions which are Th1 or Th2 mediated, including, but not limited to, asthma, allergies, allergic bronchopulmonary aspergillosis, arthritis, inflammatory diseases, inflammatory bowel disease (IBD), viral infections, various helminthic and parasitic infections, and related conditions.

II. Specific Binding Compositions

A. Antibodies

The present invention provides for the use of antibodies or binding compositions which specifically bind to CCR8 or vMIP-I. Antibodies can be raised to various CCR8 or vMIP-I proteins, including individual, polymorphic, allelic, strain, or species variants, and fragments thereof, both in their naturally-occurring (full-length) forms or in their recombinant forms. Additionally, antibodies can be raised to CCR8 or vMIP-I proteins in both their native (or active) forms or in their inactive, e.g., denatured forms. Antiidiotypic antibodies may also be used.

A number of immunogens may be selected to produce antibodies specifically reactive, or selective for binding, with CCR8 or vMIP-I proteins. Recombinant protein is a preferred immunogen for the production of monoclonal or polyclonal antibodies. Naturally-occurring protein, from appropriate sources may also be used either in pure or impure form. Synthetic peptides may also be used as an immunogen for the production of antibodies to CCR8 or vMIP-I proteins. Recombinant protein can be expressed and purified in eukaryotic or prokaryotic cells as described, e.g., in Coligan, et al. (eds.) (1995 and periodic supplements) *Current Protocols in Protein Science* John Wiley & Sons, New York, N.Y.; and Ausubel, et al (eds.) (1987 and periodic supplements) *Current Protocols in Molecular Biology*, Greene/Wiley, New York, N.Y. Naturally folded or denatured material can be used, as appropriate, for producing antibodies. Either monoclonal or polyclonal antibodies may be generated, e.g., for subsequent use in immunoassays to measure the protein, or for immunopurification methods.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the CCR8 protein or peptide of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed, if desired. See, e.g., Harlow and Lane, *Antibodies, A Laboratory Manual*; or Coligan (ed.) *Current Protocols in Immunology*. Immunization can also be performed through other methods, e.g., DNA vector immunization. See, e.g., Wang, et al,. *Virology* 228:278–284 (1997).

Monoclonal antibodies may be obtained by various techniques familiar to those skilled in the art. Typically, spleen cells from an animal immunized with a desired antigen are immortalized, commonly by fusion with a myeloma cell. See, Kohler and Milstein, *Eur. J. Immunol.* 6:511–519 (1976). Alternative methods of immortalization include transformation with Epstein Barr Virus, oncogenes, or retroviruses, or other methods known in the art. See, e.g., Doyle, et al. (eds. 1994) and periodic supplements) *Cell and Tissue Culture: Laboratory Procedures*, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. *Science* 246:1275–1281 (1989).

Antibodies or binding compositions, including binding fragments and single chain versions, against predetermined fragments of CCR8 or vMIP-I proteins can be raised by immunization of animals with conjugates of the fragments with carrier proteins as described above. Monoclonal antibodies are prepared from cells secreting the desired antibody. These antibodies can be screened for binding to normal or defective protein. These monoclonal antibodies usually bind with at least a $K_D$ of about 1 mM, more usually at least about 300 µM, typically at least about 10 µM, more typically at least about 30 µM, preferably at least about 10 µM, and more preferably at least about 3 µM or better.

In some instances, it is desirable to prepare monoclonal antibodies (mAbs) from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane, Antibodies: *A Laboratory Manual* CSH Press (1988); Goding, *Monoclonal Antibodies: Principles and Practice* (2d ed.) Academic Press, New York, N.Y. (1986); and particularly in Kohler and Milstein, *Nature* 256:495–497 (1975), which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al., *Science* 246:1275–1281 (1989); and Ward, et al. *Nature* 341:544–546 (1989). The polypeptides and antibodies of the present invention may be used with or without modification, including chimeric or humanized antibodies. Frequently, the polypeptides and antibodies are labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. *Proc. Nat'l Acad. Sci. USA* 86:10029–10033 (1989); or made in transgenic mice, see Mendez, et al. *Nature Genetics* 15:146–156. (1997)

Antibody binding compounds, including binding fragments, of this invention can have significant diagnostic or therapeutic value. These molecules can be useful as non-neutralizing binding compounds and can be coupled to toxins or radionuclides so that when the binding compound binds to the antigen, a cell expressing it, e.g., on its surface, is killed. Further, these binding compounds can be conjugated to drugs or other therapeutic agents, either directly or indirectly by means of a linker, and may effect drug targeting.

B. Other Molecules

Antibodies are merely one form of specific binding compositions. Other binding compositions, which have similar uses, include molecules that bind with specificity to CCR8 or vMIP-I, e.g., in a partner-binding fashion, an antibody-antigen interaction, or in a natural physiologically relevant protein-protein interaction, either covalent or non-covalent, e.g., proteins which specifically associate with the protein. The molecule may be a polymer, or chemical reagent. A functional analog may be a protein with structural modifications, or may be a structurally unrelated molecule, e.g., which has a molecular shape which interacts with the appropriate binding determinants.

Drug screening can be performed to identify compounds having binding affinity to CCR8, or can block the natural interaction with ligand. Subsequent biological assays can then be utilized to determine if the compound has intrinsic blocking activity and is therefore an antagonist. Likewise, a compound having intrinsic stimulating activity can signal to the cells via the CCR8 and is thus an agonist in that it simulates the activity of a ligand.

As indicated above, I-309, TCA-3 and vMIP-I are ligands for the CCR8 chemokine receptor [I-309: (Roos, et al., *J. Biol. Chem.* 272:17251–17254 (1997); and Tiffany, et al., *J. Exp. Med.* 186:165–170 (1997); GenBank M57502 and M57506), the TARC (see Imai, et al., *J. Biol. Chem.* 272:15036–15042 (1997); GenBank D43767); TCA-3: (GenBank M17957 and X52401)]. As such, mutein antagonists of these ligands, which maintain receptor binding but lack signaling may be developed and used in the practice of the invention.

Structural studies of the ligands will lead to design of new variants, particularly analogs exhibiting agonist or antagonist properties on the receptor. This can be combined with previously described screening methods to isolate muteins exhibiting desired spectra of activities.

As receptor-specific binding molecules are provided, also included are small molecules identified by screening procedures. Various ligands for the receptor have been identified. In particular, it is well known in the art how to screen for small molecules which interfere, e.g., with ligand binding to the receptor, often by specific binding to the receptor and blocking of binding by the natural ligand. See, e.g., Meetings on High Throughput Screening, International Business Communications, Southborough, Mass. 01772–1749. Such molecules may compete with natural ligands, and selectively bind to the CCR8. Such specific binding compounds may be labeled or conjugated to toxic reagents, which are targeted to CCR8+ cells. These specific binding reagents may similarly be -used to target Th2 cells.

III. Immunoassays

Immunoassays are. valuable in diagnosing a disease or disorder associated with Th2 imbalance or pathology. Qualitative or quantitative measurement of a particular protein such as CCR8, which has been shown to be preferentially expressed on Th2 cells can be performed by a variety of immunoassay methods. For a review of immunological and immunoassay procedures in general, see Stites and Terr (eds.) *Basic and Clinical Immunology* (7th ed.) (1991). Moreover, the immunoassays of the present invention can be performed in many configurations, which are reviewed extensively in Maggio, Enzyme Immunoassay CRC Press, Boca Raton, Fla. (ed. 1980); Tijan, "Practice and Theory of Enzyme Immunoassays," Laboratory *Techniques in Biochemistry and Molecular Biology*, Elsevier Science Publishers B.V., Amsterdam; and Harlow and Lane, *Antibodies, A Laboratory Manual*, (1985) supra. See also Chan, Immunoassay: *A Practical Guide Academic* Press, Orlando, Fla. (ed. 1987); *Price, Principles and Practice of Immunoassays* Stockton Press, N.Y. Newman (eds. 1991); and Ngo, *Nonisotopic Immunoassays Plenum* Press, N.Y. (ed. 1988).

Immunoassays for measurement of CCR8 proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably, the capture agent is an antibody specifically reactive with CCR8 proteins produced as described above. The concentration of labeled analyte bound to the capture agent is inversely proportional to the amount of free analyte present in the sample.

In a competitive binding immunoassay embodiment of the invention, the CCR8 protein present in the sample competes with labeled protein for binding to a specific binding agent, for example, an antibody specifically reactive with the CCR8 protein. The binding agent may be bound to a solid surface to effect separation of bound labeled protein from the unbound labeled protein. Alternately, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

CCR8 proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of CCR8 proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above may employ labeled assay components. The label may be coupled directly or indirectly to the desired component of the assay according to methods well-known in the art. A wide variety of labels and methods may be used. Traditionally, a radioactive label incorporating $^3$H, $^{125}$I, $^{35}$S, $^{14}$C, or $^{32}$P was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904.

Antibodies reactive with a particular protein can also be measured by a variety of immunoassay methods. Thus modifications of the above procedures may be used to determine the amounts or affinities of various CCR8 antibodies or antibody preparation. For a review of immunological and immunoassay procedures applicable to the measurement of antibodies by immunoassay techniques, see Stites and Terr (eds.), *Basic and Clinical Immunology* (7th ed.) supra; Maggio (ed.), *Enzyme Immunoassay*, supra; and Harlow and Lane, *Antibodies, A Laboratory Manual*, supra.

Screens to evaluate the binding and activity of monoclonal antibodies and binding compositions encompass a variety of methods. Binding can be assayed by detectably labeling the antibody or binding composition as described above. Cells expressing a CCR8 receptor are incubated with this antibody or binding composition, and binding is assayed by Fluorescence Activated Cell Sorting (FACS) analysis.

To evaluate Th2 depletion ability, experimental animals, e.g., mice, are preferably induced to produce those cell types, e.g., by infection with a parasite. Th2 cell counts are made prior to and at various time points after administration of a bolus of the candidate depleting monoclonal antibody or binding composition. Levels are analyzed in various samples, e.g., blood, serum, nasal or pulmonary lavages, or tissue biopsy staining. A successful depleting mAb or binding composition significantly lowers the level of circulating Th2 cells. Thus, a substantially pure or depleted population is at least about 85% pure, more preferably at least about 90% pure, and even more preferably at least about 95, 97, or 99% pure.

Evaluation of antibodies can be performed in other animals, e.g., humans using various methods. For example, blood samples are withdrawn from patients suffering from a Th2 related disease or disorder before and after treatment with a candidate antibody. The antibodies can be used in a diagnostic context to evaluate the extent of Th1 or Th2 polarization, e.g., by FACS, tissue staining, in vitro culture.

IV. Uses

The present invention is useful in the treatment of medical conditions or diseases associated with a Th1 or Th2 cell imbalance. See, e.g., Frank, et al., (eds.1995) *Samter's Immunologic Diseases*, 5th Ed., vols. I-II, Little, Brown and Co., Boston, Mass.; Coffman, et al., *Science* 245:308–310 (1989); and Frick, et al., *J. Allergy Clin. Immunol.* 82:199–225 (1988); each of which is incorporated herein by reference. The binding specificities of the compositions described herein can be administered alone or in combination with another modulator of Th balance, including, e.g., IFN-γ, IL-2, IL-4, antagonists, or other compounds used for the treatment of symptoms, e.g., steroids such as glucocorticoids.

In particular, the selectivity of the CCR8 receptor on these cell types of the CD4+ lineage provides a means to block the functions of the respective cell types. The expression appears on the CD4+CD8+ subset (double positive or DP). See Zinoni, et al., *J.Immunol.* 161:547–551 (1998), incorporated herein by reference. The expression in this subset may correspond to cells that have already undergone positive selections and are destined, e.g., committed, to become CD4+ thymocytes. As I-309 has been reported to prevent apoptosis in a thymoma (Van Snick, et al., *J. Immunol.* 157:2570–2576 (1996)), the CCR8 may be involved in positive selection in the double positive subset in T cell development. Ligands which agonize or antagonize this reaction may have importance in the regulation of apoptosis in T cell development, as well as Th2 or Th1 dominant response shifting. vMIP-I or other CCR8 agonists may therefore be used to activate, initiate, or strengthen Th2 mediated responses. Alternatively, these antagonists may block the recruitment or attraction of CCR8+ cells to the sites of ligand production, e.g., to the lung or other sites of allergic or asthmatic effects, or to block activation or maintenance of Th2 signaling through the CCR8 receptor. In a like manner, CD8+ cytotoxic T cells may also have a similar developmental pathway. See O'Garra and Murphy, *Curr. Opinion in Immunol.* 6:458–466 (1994); Palliard, et al., *J. Immunol.* 141:849–855 (1988); Erard, et al., *Science* 260:1802–1805 (1993).

For example, CCR8 ligands, such as vMIP-I, specifically signal the cell types expressing the receptor. Thus, it may be desirable to block signaling to the Th2 subsets by reagents which block receptor signaling, e.g., antibodies to receptor, antibodies to ligand, and small drug antagonists. The knowledge of the CCR8 mediation of Th2 trafficking and the CCR8/vMIP-I interaction provide means to block the attraction by the CCR8 ligands.

Particular medical conditions which are Th1 or Th2 mediated, and are subject to treatment with this invention include, e.g., asthma, allergies, allergic bronchopulmonary aspergillosis, arthritis, inflammatory diseases, IBD, topic dermatitis, viral infections, various helminthic and parasitic infections, and related conditions. See, e.g., Frank, et al., Samter's *Immunologic Diseases*, 5th Ed., vols. I-II (eds.1995), Little, Brown and Co., Boston, Mass.; Coffman, et al., *Science* 245:308–310 (1989); and Frick, et al., *J. Allergy Clin. Immunol.* 82:199–225 (1988).

Conversely, it may be desirable to use known ligands to selectively affect specific functions mediated by Th2 cells. Thus, positive effects, e.g., blocking of apoptotic signals to these cell types becomes feasible. There exists some evidence that I-309 can signal an anti-apoptotic signal. Thus, antagonists of the ligands may block the protection, resulting in cell death. Conversely, blocking of attractive signals to CCR8+ cells may be effected.

Standard immunological techniques are described, e.g., in Hertzenberg, et al., *Weir's Handbook of Experimental Immunology* vols 1–4, Blackwell *Science (eds.* 1996); Coligan, *Current Protocols in Immunology* Wiley/Greene, NY (1991); and *Methods in Enzymology* volumes 70, 73, 74, 84, 92, 93, 108, 116, 121, 132, 150, 162, and 163. These techniques are readily available in the art and allow use of the reagents for purifying cell subpopulations.

To prepare pharmaceutical or sterile compositions including the CCR8 specific binding composition, the antibody or binding composition is admixed with a pharmaceutically acceptable carrier or excipient which is preferably inert. Preparation of such pharmaceutical compositions is known in the art, see, e.g., *Remington's Pharmaceutical Sciences and U.S. Pharmacopeia: National Formulary*, Mack Publishing Company, Easton, Pa. (1984).

Antibodies or binding compositions are normally administered parenterally, preferably intravenously. Since such protein or peptide antagonists may be immunogenic they are preferably administered slowly, either by a conventional IV administration set or from a subcutaneous depot, e.g. as taught by Tomasi, et al., U.S. Pat. No. 4,732,863.

When administered parenterally the antibodies or fragments are formulated in a unit dosage injectable form (solution, suspension, emulsion) in association with a pharmaceutically acceptable parenteral vehicle. Such vehicles are inherently nontoxic and nontherapeutic. The antagonist may be administered in aqueous vehicles such as water, saline or buffered vehicles with or without various additives and/or diluting agents. Alternatively, a suspension, such as a zinc suspension, can be prepared to include the peptide. Such a suspension can be useful for subcutaneous (SQ) or intramuscular (IM) injection. The proportion of antagonist and additive can be varied over a broad range so long as both are present in effective amounts. The antibody is preferably formulated in purified form substantially free of aggregates, other proteins, endotoxins, and the like, at concentrations of about 5 to 30 mg/ml, preferably 10 to 20 mg/ml. Preferably, the endotoxin levels are less than 2.5 EU/ml. See, e.g., Avis, et al. (eds.) (1993) *Pharmaceutical Dosage Forms: Parenteral Medications* 2d ed., Dekker, NY; Lieberman, et al., (eds.) (1990) *Pharmaceutical Dosage Forms: Tablets* 2d ed., Dekker, NY; Lieberman, et al., (eds.)(1990) *Pharmaceutical Dosage Forms: Disperse Systems* Dekker, NY; Fodor, et al., *Science* 251:767–773 (1991); Coligan (ed.), *Current Protocols in Immunology*; Hood, et al., *Immunology* Benjamin/Cummings; Paul (ed.) *Fundamental Immunology*; Academic Press; Parce, et al., *Science* 246:243–247 (1989); Owicki, et al., *Proc. Nat'l Acad. Sci. USA* 87:4007–4011 (1990); and Blundell and Johnson, *Protein Crystallography*, Academic Press, New York (1976).

Selecting an administration regimen for an antagonist depends on several factors, including the serum or tissue turnover rate of the antagonist, the level of Th2 depletion, the immunogenicity of the antagonist, the accessibility of the target Th2 cells (e.g., if non-serum Th2 cells are to be blocked). Preferably, an administration regimen maximizes the amount of antagonist delivered to the patient consistent with an acceptable level of side effects. Accordingly, the amount of antagonist delivered depends in part on the particular antagonist and the severity of the condition being treated. Guidance in selecting appropriate doses is found in the literature on therapeutic uses of antibodies, e.g. Bach et al., chapter 22, in Ferrone et al., (eds.) (1985), *Handbook of Monoclonal Antibodies Noges Publications*, Park Ridge, N.J.; and Russell, pgs. 303–357, and Smith et al., pgs. 365–389, in Haber, et al., (eds.) (1977) *Antibodies in Human Diagnosis and Therapy*, Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. Circulating activated Th2 levels are important indicators of when an effective dose is reached. Preferably, a CCR8 antibody or binding composition thereof that is used is derived from the same species as the animal targeted for treatment, thereby minimizing a humoral response to the reagent.

The total weekly dose ranges for antibodies or fragments thereof range generally from about 1 $\mu$g, more generally from about 10 ng, typically from about 100 ng; more typically from about 1 $\mu$g, more typically from about 10 $\mu$g, preferably from about 100 $\mu$g, and more preferably from about 1 mg per kilogram body weight. Although higher amounts may be more efficacious, the lower doses typically will have fewer adverse effects. Generally the range is less than 100 mg, preferably less than about 50 mg, and more preferably less than about 25 mg per kilogram body weight.

The weekly dose ranges for antagonists, e.g., antibody, binding fragments, range from about 10 $\mu$g, preferably at least about 50 $\mu$g, and more preferably at least about 100 $\mu$g per kilogram of body weight. Generally, the range is less than about 1000 $\mu$g, preferably less than about 500 $\mu$g, and more preferably less than about 100 $\mu$g per kilogram of body weight. Dosages are on a schedule which effects the desired treatment and can be periodic over shorter or longer term. In general, ranges are from at least about 10 μg to about 50 mg, preferably about 100 μg to about 10 mg per kilogram body weight.

Other antagonists of the ligands, e.g., muteins, are also contemplated. Hourly dose ranges for muteins range from at least about 10 μg, generally at least about 50 mg, typically at least about 100 mg, and preferably at least 500 mg per hour. Generally the dosage is less than about 100 mg, typically less than about 30 mg, preferably less than about 10 mg, and more preferably less than about 6 mg per hour. General ranges are from at least about 1 μg to about 1000 μg, preferably about 10 μg to about 500 μg per hour.

The present invention also provides for administration of CCR8 or ligand antibodies or binding compositions in combination with known therapies, e.g., steroids, particularly glucocorticoids, which alleviate the symptoms associated with excessive Th1 or Th2 responses. Daily dosages for glucocorticoids range from at least about 1 mg, generally at least about 2 mg, and preferably at least about 5 mg per day. Generally, the dosage will be less than about 100 mg, typically less than about 50 mg, preferably less than about 20 mg, and more preferably at least about 10 mg per day. In general, the ranges are from at least about 1 mg to about 100 mg, preferably from about 2 mg to 50 mg per day.

The phrase "effective amount" means an amount sufficient to ameliorate a symptom or sign of the Th1 or Th2 condition. Typical mammalian hosts include mice, rats, cats, dogs, and primates, including humans. An effective amount for a particular patient may vary depending on factors such as the condition being treated, the overall health of the patient, the method, route, and dose of administration and the severity of side affects. When in combination, an effective amount is in ratio to a combination of components and the effect is not limited to individual components alone.

An effective amount of antagonist decreases the symptoms typically by at least about 10%; usually by at least about 20%; preferably at least about 30%; or more preferably at least about 50%. The present invention provides reagents which find use in therapeutic applications as described elsewhere herein, e.g., in the general description for treating disorders associated with Th1/Th2 imbalances. See, e.g., Berkow (ed.), *The Merck Manual of Diagnosis and Therapy*, Merck & Co., Rahway, N.J.; Thorn, et al., Harrison's *Principles of Internal Medicine*, McGraw-Hill, NY; Gilman, et al., (eds.) (1990) Goodman and Gilman's: *The Pharmacological Bases of Therapeutics*, 8th Ed., Pergamon Press; *Remington's Pharmaceutical Sciences*, 17th ed. (1990), Mack Publishing Co., Easton, Penn; Langer, *Science* 249:1527–1533 (1990); and Merck Index, Merck & Co., Rahway, N.J.

Antibodies to CCR8 proteins may be used for the identification or sorting of cell populations expressing CCR8 protein, e.g., activated T helper cells. Methods to sort such populations are well known in the art, see, e.g., Melamed, et al., (1990) *Flow Cytometry* and Sorting Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y. Populations of cells expressing the CCR8 receptor can also be purified using magnetic beads as described, e.g., in Bieva, et al., *Exp. Hematol.* 17:914–920 (1989); Hernebtub, et al., *Bioconj. Chem.* 1:411–418 (1990); Vaccaro, *Am. Biotechnol. Lab.* 3:30 (1990).

Moreover, antisense nucleic acids may be used. For example, antisense against the ligands may function in a manner similar to ligand antagonists, and antisense against the CCR8 receptor may function similar to receptor antagonists. Thus, it may be possible to block signaling with antisense nucleic acids. Conversely, nucleic acids for the receptor may serve as agonists, increasing the numbers of receptors on the cell, thereby increasing cell sensitivity to ligand, and perhaps blocking the normal apoptotic signal described.

Using the assay methods described above, the antibodies or binding compositions are useful in diagnosing disease states which result in Th1 or Th2 imbalances. Labeled antibodies can also be utilized in analyzing Th2 infiltration in tissues. Antibodies raised against each CCR8 protein are also useful to raise anti-idiotypic antibodies. These antibodies are useful in detecting or diagnosing various immunological conditions related to expression of the respective antigens. Combinations of these signals may. be also pursued.

The broad scope of this invention is best understood with reference to the following examples, which are not intended to limit the inventions to the specific embodiments.

EXAMPLES

I. General Methods

Some of the standard methods are described or referenced, e.g., in Maniatis, et al., *Molecular Cloning, A Laboratory Manual*, Cold Spring Harbor Laboratory, Cold Spring Harbor Press (1982); Sambrook, et al., *Molecular Cloning: A Laboratory Manual*, (2d ed.), vols. 1–3, CSH Press (1989),; Ausubel, et al., *Biology*, Greene Publishing Associates, Brooklyn, N.Y. NY; or Ausubel, et al. *Current Protocols in Molecular Biology*, Greene/Wiley, New York (1987) and Supplements); Innis, et al. (eds.) *PCR Protocols: A Guide to Methods and Applications Academic Press*, N.Y. (1990). Methods for protein purification include such methods as ammonium sulfate precipitation, column chromatography, electrophoresis, centrifugation, crystallization, and others. See, e.g., Ausubel, et al. (and periodic supplements) 1987, supra; Deutscher "Guide to Protein Purification" in *Methods in Enzymology*, vol. 182 (1990), and other volumes in this series; manufacturer's literature on use of protein purification products, e.g., Pharmacia, Piscataway, N.J., or Bio-Rad, Richmond, Calif.; and Coligan, et al. (eds.) (and periodic supplements) *Current Protocols in Protein Science*, John Wiley & Sons, New York, N.Y. (1995). Combination with recombinant techniques allow fusion to appropriate segments, e.g., to a FLAG sequence or an equivalent which can be fused via a protease-removable sequence. See, e.g., Hochuli, *Chemische Industrie* 12:69–70 (1989); Hochuli, "Purification of Recombinant Proteins with Metal Chelate Absorbent" in Setlow (ed.) *Genetic Engineering*, Principle and Methods 12:87–98 (1990), Plenum Press, N.Y.; and Crowe, et al., QIAexpress: *The High Level Expression & Protein Purification System* QIAGEN, Inc., Chatsworth, Calif. (1992).

Standard immunological techniques are described, e.g., in Hertzenberg, et al. (eds.) *Weir's Handbook of Experimental Immunology* vols 1–4 (1996), Blackwell Science; Coligan, *Current Protocols in Immunology* Wiley/Greene, NY (1991); and *Methods in Enzymology* volumes. 70, 73, 74, 84, 92, 93, 108, 116, 121, 132, 150, 162, and 163. Methodology of cell biology techniques are described, e.g., in Celis (ed.) *Cell Biology: A Laboratory Handbook* Academic Press, San Diego (1998); and Doyle, et al. (eds. and periodic supplements) *Cell and Tissue Culture: Laboratory Procedures*, John Wiley and Sons, New York, N.Y. (1994).

Techniques in developmental systems are described, e.g., in Meisami (ed.), *Handbook of Human Growth and Developmental Biology* CRC Press; and Chrispeels (ed.), *Molecular Techniques and Approaches in Developmental Biology Interscience*.

FACS analyses are described in Melamed, et al., *Flow Cytometry and Sorting* Wiley-Liss, Inc., New York, N.Y. (1990); Shapiro (1988) Practical Flow Cytometry Liss, New York, N.Y.; and Robinson, et al., *Handbook of Flow Cytometry Methods* Wiley-Liss, New York, N.Y. (1993).

II. Isolation of mammalian CCR8 encoding sequences

The human CCR8 sequence is readily available. See, e.g., Roos, et al., *J. Biol. Chem.* 272:17251–17254 (1997); and Tiffany, et al., *J. Exp. Med.* 186:165–170 (1997); GenBank Accession Numbers AF005210 and U45983. See also WO 96/39434.

To isolate the mouse sequence, a 1057 bp fragment containing the entire ORF of the human CCR8 gene was used as probe to screen the murine 129/SV genomic library in the l/fix vector (Stratagene, La Jolla, Calif.). 350,000 phage clones were plated. Hybridization with the labeled human CCR8 cDNA was carried out at 370° C. in 50% formamide, 5× SSPE, 10× Denhardt's, 0.1% SDS, and 100 mg/ml salmon sperm DNA for 16 hrs. Filters were washed three times at 500° C. in 2× SSC, 0.1% SDS, 20 min. each. Positive genomic phage clones were isolated according to the plaque purification procedure. DNA was extracted, digested by restriction endonucleases, and Southern blot analysis was performed. Hybridizing restriction fragments were subcloned in the pGem11 plasmid (Promega) and sequenced using Sequenase 2.0 (USB). DNA sequence analysis was performed using the DNAsis/Prosis software (Hitachi).

III. Production of Cell Lines

CCR2, CCR6, CCR7 and CCR9 were stably expressed in murine BaF/3 cells [Palacios, et al. , *Nature* 391: 86–89 (1984)] using a murine retroviral sysem [Kitamura, et al., *Proc. Natl. Acad. Sci. USA* 92: 9146–50 (1995)]. CCR8 was stably expressed in rat Y3 cells (ATCC CRL-1631) using PME-18S-neo. CCR5, XCR1, GPR9-6, and STRL33 were stably expressed in human embryonic kidney (HEK) 293 cells (ATCC CRL-1573) using PCDNA3.1 (Invitrogen). All lines were maintained in appropriate culture medium (RPMI or DMEM, 10% FCS, 10 µg/ml IL-3 for BaF/3 cells) containing 1 mg/ml G418 (Gibco) and were periodically tested for their ability to flux calcium in response to known ligands. Y3 cells are prepared in culture medium (RPMI of 10% FCS). Transfected cells also contain 1 mg/ml G418.

Other methods of evaluation of expression can also be utilized, e.g., staining and FACS analysis, tissue staining, Northern analysis, etc.

Similarly, the ligands can be recombinantly produced, purchased, or fragments synthetically produced. The ligands will be useful in generating further mutein antagonists or antibodies blocking their effector functions.

IV. CCR8 Antibody Production

Appropriate mammals are immunized with appropriate amounts of CCR8 transfected cells, e.g., intraperitoneally every 2 weeks for 8 weeks. Typically, rodents are used, though other species should accommodate production of selective and specific antibodies. The final immunization is given intravenously (IV) through the tail vein.

Generic polyclonal antibodies may be collected. Alternatively, monoclonal antibodies ("mAbs") can be produced. For example, four days after the IV injection, the spleen is removed and fused to SP2/0 and NS1 cells. HAT resistant hybridomas are selected e.g., using a protocol designed by Stem Cell Technologies (Vancouver, BC). After 10 days of HAT selection, resistant foci are transferred to 96 well plates and expanded for 3 days. Antibody containing supernatants are analyzed, e.g., by FACS for binding to NIH3T3/CCR8 transfectants. Many different CCR8 mAbs are typically produced. Those antibodies may be isolated and modified, e.g., by labeling or other means as is standard in the art. See, e.g., Harlow and Lane, *Antibodies: A Laboratory Manual* CSH Press (1988); Goding, *Monoclonal Antibodies: Principles and Practice* (2d ed.) Academic Press, New York, N.Y. (1986). Methods to conjugate magnetic reagents, toxic entities, labels, attach the antibodies to solid substrates, to sterile filter, etc., are known in the art.

Additionally, some of the mAbs are used to sort CCR8 positive cells in spleens from mice or primates. Various treatments of the mice are evaluated to determine the relative proportions of Th1 and Th2 cells.

V. CCR8 Antagonists

Various antagonists of the CCR8 are available. For example, antibodies. against the receptor itself may block the binding of ligand, thereby serving as a direct receptor antagonist. Other antagonists may function by blocking the binding of ligand to receptor, e.g., by binding to the ligand in a way to preclude the possibility of binding to the receptor. Other antagonists, e.g., mutein antagonists, may bind to the receptor without signaling, thereby blocking a true agonist from binding. Many of these may serve to block the signal transmitted to the CCR8 bearing cells, specifically Th2 cells. Thus, means are provided to block physiological signals transduced through CCR8, which is selectively expressed-on Th2 cells.

In addition, the CCR8 specific reagents are useful in targeting CCR8+ cells, which are also cells. Thus, toxic conjugates selectively deplete CCR8+ cells from a population. This treatment is useful in treating parasitic infections, which typically involve a cellular response (Th1 type). The deletion of Th2 cells removes the accompanying suppression of Th1 effector functions.

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

Example I

This example shows identification of CCR8 as a specific host-encoded receptor for vMIP-I In order to determine the host-encoded receptor(s) for vMIP-I cell lines stably transfected with known or suspected chemokine receptors were screened for calcium flux in response to vMIP-I and other chemokines. vMIP-I and chemokines were obtained commercially (R&D Systems, Minneapolis, Minn. or Peprotech, Rocky Hill, N.J.) or produced by DNAX/Schering-Plough.

BaF/3 cells were loaded with Fluo-3-AM (Sigma Chemical) in appropriate culture medium (RPMI or DMEM/ 10% serum) for 1 h at 37° C. after which cells were washed 3× in flux buffer (Hank's balanced salt solution, 20 mM HEPES, 0.1BSA) and aliquoted into a 96-well black-walled plates at a density of $1 \times 10^5$ cells/well. HEK 293 and Y3 cells were plated at a density of $5 \times 10^4$ cells/well one day in advance of assaying, loaded for one hour in culture medium as above and washed four times. All plates were pre-coated with poly-L-lysine. Calcium flux was measured in all 96-wells simultaneously and in real time using a Fluorescent Imaging Plate Reader (FLIPR; Molecular Devices, Sunnyvale, Calif.) and data expressed as fluoroscience units vs. time.

Y3 rat myeloid cells expressing exogenous human CCR8 (CCR8-Y3) were analyzed for reponsiveness to a variety of chemokines by measuring calcium flux in response to ligand stimulation. The results are provided in Tables 1 and 2.

TABLE I

Chemokines which induce a calcium flux in CCR8- Y3 cells.

| Chemokine | Response | Chemokine | Response |
|---|---|---|---|
| MCP-1 | − | MIP-4 | − |
| MCP-2 | − | mC10 | − |
| MCP-3 | − | I-309 | ++ |
| MCP-4 | − | TECK | − |
| mMCP-5 | − | mTECK | − |
| Eotaxin | − | Mig | − |
| MIP-1a | − | IP-10 | − |
| MIP-1b | − | vMIP-I | ++ |
| DC-CK-1 | − | SDF-1a | ++ (also in negative control) |
| RANTES | − | SDF-1b | ++ (also in negative control) |
| HCC-1 | − | Fractalkine | − (soluble domain of Fractalkine) |
| mMIP-1g | − | IL-8 | − |
| 6Ckine | | mJE | − |
| m6Ckine | − | GROa | − |
| BCA-1 | − | ENA-78 | − |
| MIP-3a | − | mLptn | − |
| MIP-3b | − | NAP-2 | − |
| TARC | − | mGCP-2 | − |
| MDC | − | mLIX | − |
| | | mMIP-2 | − |

All chemokine tested were human unless otherwise denoted by "m" prefix. SDF-1a/b signaling is the result of endogenous CXCR4 on Y3 cells and was present in parental (CCR8-) line.

TABLE 2 vMIP-I induced calcium flux in CCR8- Y3 cells is dose-dependent

| [vMIP-I] nM | Relative Calcium Flux |
|---|---|
| 100 | ++++ |
| 10 | ++++ |
| 1.0 | +++ |
| 0.1 | ++ |

TABLE 2-continued vMIP-I induced calcium flux in CCR8- Y3 cells is dose-dependent

| [vMIP-I] nM | Relative Calcium Flux |
|---|---|
| 0.01 | + |
| 0 | − |

Y3-CCR8 cells were stimulated with the indicated concentration of vMIP-I.
Relative peak calcium flux is indicated.

Among the various chemokines tested (all at 10 nM), only I-309 and vMIP-I resulted in a calcium flux. These same cells also responded to I-309, but not to any of thirty-nine other chemokines tested. The calcium response to vMIP-I was dose-dependent and observable at picomolar concentrations. Prior incubation of CCR8-Y3 cells with vMIP-I also inhibited subsequent signaling to I-309 in a dose-dependent manner. See Table 3 below. Similarly, I-309 stimulation blocked subsequent signaling to vMIP-I. See Table 4 below. The response of CCR8-Y3 cells to SDF-1a and SDF-1b (Table 1) was also observed in Y3 cells transfected with the orphan chemokine receptor human chemokine receptor, (HCR) [Fan, et al. , Biochem. Biophys. Res. Commun. 243:264–8 (1998)]/LPS inducible chemokine recepor (L-CCR) [Shimada, et al., FEBS Lett 425:490–4 (1998)] which were not responsive to either vMIP-I or I-309. Parental Y3 cells also responded to SDF-la , but not vMIP-I or I-309. Twelve other receptors tested including CCR2, CCR3, CCR5, CCR6, CCR7, CCR9, CXCR3, CXCR4, XCR1, GPR9-6, STRL33, and HCR/L-CCR, also failed to respond to vMIP-I or I-309 with a calcium flux despite being responsive to their known ligands.

TABLE 3 vMIP-I cross-desensitization cf I-309 signaling in CCR8-Y3 cells.

| [vMIP-I] nM | [I-309] nM | Relative Calcium Flux |
|---|---|---|
| 0 | 0 | − |
| 0 | 10 | ++++ |
| 0.01 | 10 | +++ |
| 0.1 | 10 | ++ |
| 1.0 | 10 | + |
| 10 | 10 | +/− |

CCR8-Y3 cells were stimulated with the indicated concentration of vMIP-I for three minutes prior to a second stimulation with I-309 at the indicated concentration.
Relative peak calcium flux is indicated.

TABLE 4

I-309 cross-desensitization of vMIP-I signalling in CCR8-Y3 cells.

| [I-309] nM | [vMIP-I] nM | Relative Calcium Flux |
|---|---|---|
| 0 | 0 | − |
| 0 | 10 | ++++ |
| 0.01 | 10 | +++ |
| 0.1 | 10 | ++ |
| 1.0 | 10 | + |
| 10 | 10 | +/− |

CCR8-Y3 cells were stimulated with the indicated concentration of I-309 for three minutes prior to a second stimulation with vMIP-I at the indicated concentration.
Relative peak calcium flux is indicated.

Example II

This example provides evidence that vMIP-I desensitizes subsequent CCR8 responses to I-309 and vice versa.

The ability of vMIP-I to compete for $^{125}$I-labeled I-309 binding to CCR8-Y3 cells was examined. CCR8-Y3 cells were resuspended in binding buffer (125 mM NaCl, 25 mM HEPES, 1 mM CaCl$_2$, 5 mM MgCl$_2$, 0.5% BSA, pH 7.0; 200,000 cells kn 200 ml) with 0.1 nM [$^{125}$I]-I-309 (100,000 cpm). Unlabelled vMIP-I and I-309 were included as competitors where indicated. Reactions were incubated at room temperature for three to five hours, harvested (Unifilter-96y Harvester, Packard Instrument Co., Meriden, Conn.) onto 96-well GF/C filter plates (Packard) and washed with 4° C. binding buffer containing 500 mM NaCl. The filter plates were dried at room temperature overnight, scintillation cocktail (Microscint-0, Packard) was added and plates were counted (Topcount HTGS, Packard). Data was analyzed by non-linear regression (GraphPad Prism, GraphPad Software, Inc., San Diego, Calif.) and is expressed as the average of triplicates (±standard deviation).

Figure 1:
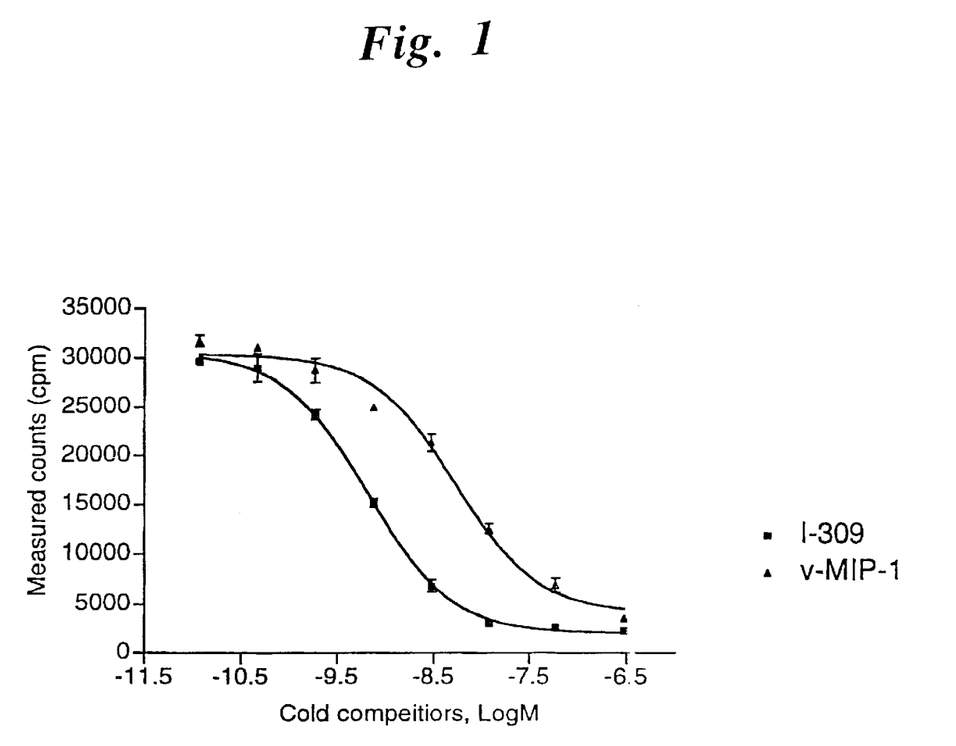
FIG. 1 shows the results of a competition binding assay of recombinant I-309 or vMIP-I as assessed on CCR8-Y3 whole cells. Kd for I-309=0.65±0.17 nM (n=2) and Ki for vMIP-I=4.68±0.44 nM (n=2). Results are expressed as total counts vs. log concentraton of competitor.

As shown in FIG. 1, vMIP-I compete successfully for I-309 binding to CCR8-Y3 cells with an $K_i$ of 4.68±0.44 nM which was somewhat higher (7-fold) than the $K_d$ observed for I-309 binding (0.65±0.17 nM). Saturation binding of I-309 to CCR8-Y3 cells showed a $K_d$ of 0.40±0.23 nM (n=5). Interestingly, the $EC_{50}$ for CCR8-Y3 cell calcium response was roughly equivalent for vMIP-I and I-309 stimulation (~3.7 nM).

Example III

This example demonstrates the biological activity of vMIP-I.

In vitro chemotaxis assays were performed to determine whether vMIP-I binding to CCR8-Y3 cells could also mediate a down-stream biologic response in a 48-well microchemotaxis chamber. [Hedrick, et al., *J. Immunol.* 158: 1533–40 (1997)] using PVDP0-free porous membranes (5μm pore size). Assays were conducted over a one hour period and cells were counted in an automated fashion using public domain NIH Image analysis software (developed at the U.S. Natl. Inst. of Health and available at http://rsb.info.nih.gov/nih.image). Five high power (400×) fields were counted for each of duplicate wells of a stated concentration.

Figure 2:
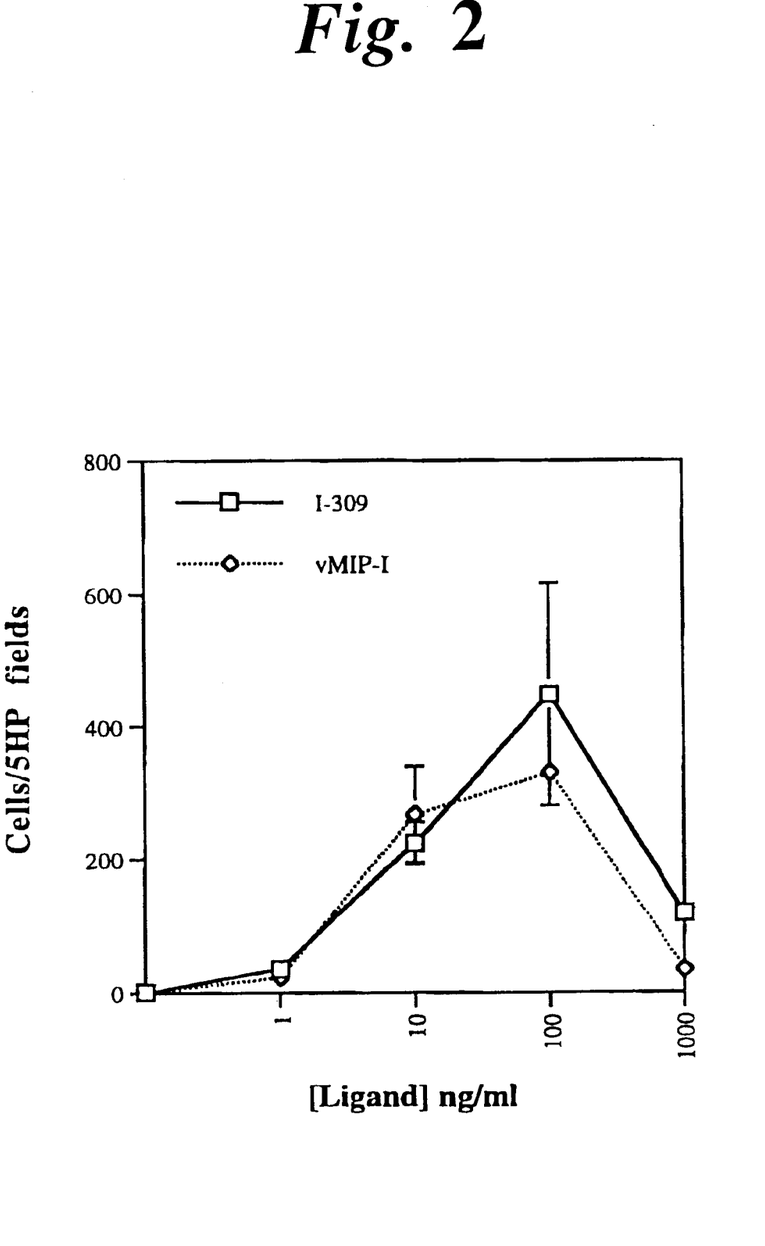
FIG. 2 shows the chemotactic response of CCR8-Y3 cells to either vMIP-I or I-309, as measured in the 48-well microchemotaxis assay. Results are shown as number of cells migrating/five high power (400×) fields vs. concentration of ligand. The results are representative of two independent experiments and each data point is the average of duplicate wells. Vehicle alone served as a negative control.

CCR8-Y3 cells were found to respond vigorously to both vMIP-I and I-309 (FIG. 2). This response showed the typical bell-shaped curve previously observed in microchemotaxis assays and was maximal at 10 nM for both vMIP-I and I-309. Background migration in this assay system was essentially zero with fewer than five cells/5 high power fields migrating in response to medium alone. These data demonstrate that vMIP-I acts as a CCR8 agonist for chemotaxis as well as calcium flux and that vMIP-I is effective in attracting host cells in vivo.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method for modulating binding of T-helper cells to a CCR8 ligand comprising contacting said cells with viral macrophage inflammatory protein I (vMIP-I).

2. The method of claim 1, wherein said CCR8 ligand is I-309.

3. The method of claim 2, wherein said I-309 is radiolabeled with $^{125}$I.

4. A method for modulating calcium flux in T-helper cells comprising contacting said cells with viral macrophage inflammatory protein I (vMIP-I).

5. A method for mediating T-helper cell chemotaxis comprising contacting said cells with viral macrophage inflammatory protein I (vMIP-I).

6. The method of claim 5, wherein the concentration of vMIP-I is 10 nm.

* * * * *